United States Patent
Trettenero

(12) 
(10) Patent No.: US 6,364,665 B1
(45) Date of Patent: Apr. 2, 2002

(54) DENTAL WHITENING KIT AND METHOD OF USING SAME

(76) Inventor: D. Scott Trettenero, 5050 Harborage Dr., Fort Myers, FL (US) 33908

(*) Notice: Subject to any disclaimer, the term of this patent is extended or adjusted under 35 U.S.C. 154(b) by 0 days.

(21) Appl. No.: 09/542,262

(22) Filed: Apr. 4, 2000

(51) Int. Cl.⁷ .................................................. A61C 5/00
(52) U.S. Cl. ............................................................ 433/215
(58) Field of Search ................................ 433/215, 214, 433/6, 37, 216

(56) References Cited

U.S. PATENT DOCUMENTS

| | | | |
|---|---|---|---|
| 1,763,553 A | * 6/1930 | Dennis | 433/6 |
| 3,379,193 A | * 4/1968 | Monaghan | 433/6 |
| 3,688,406 A | * 9/1972 | Porter et al. | 433/6 |
| 4,776,792 A | * 10/1988 | Wagner et al. | 433/37 |
| 5,011,407 A | * 4/1991 | Peleria | 433/37 |
| 5,076,791 A | * 12/1991 | Madray, Jr. | 433/216 |
| 5,769,633 A | * 6/1998 | Jaobs et al. | 433/37 |

\* cited by examiner

*Primary Examiner*—Todd E. Manahan
(74) *Attorney, Agent, or Firm*—William E. Noonan

(57) ABSTRACT

A dental whitening kit is used to apply a tooth whitening composition to a user's teeth. The kit includes a mouthpiece having a cavity for receiving the teeth and a separate and distinct thin sheet composed of a heat and pressure deformable plastic. The sheet is heated to a temperature and for a duration such that the sheet is sufficiently pliable to form a dental impression therein. The sheet is disposed over the cavity such that the user bites into the sheet and the cavity to form a tray having an impression of the user's teeth. The tray and the mouthpiece are disengaged from the teeth. The tray is then separated from the cavity of the mouthpiece and receives the tooth whitening composition. The user re-engages into the tray with the teeth to apply the whitening composition to the teeth.

14 Claims, 6 Drawing Sheets

DENTAL WHITENING KIT AND METHOD OF USING SAME

FIELD OF THE INVENTION

This invention relates to a kit for whitening a user's teeth, as well as a method for utilizing such a dental whitening kit.

BACKGROUND OF THE INVENTION

Cosmetic dental whitening is becoming increasingly popular. Traditionally, most whitening of the teeth has been performed at the dentist's office. Initially, an impression is made of the patient's teeth and a laboratory quality gel tray is manufactured from that impression. This procedure is fairly labor and time intensive. First the dentist must take the impression. Next, the tray must be manufactured by a technique such as vacuuforming. The patient then returns to the dentist's office to determine if the tray fits properly. Only then can the actual whitening procedure commence. Professional dental whitening is typically quite expensive for the patient. Costs often range between $300–$650. The process is also time consuming for the dentist and his or her staff. Expensive equipment normally must be purchased to manufacture the gel trays.

Recently, inexpensive "at home" dental whitening kits have become available. These products usually comprise a bulky mouthpiece which resembles a sports mouth guard. The user purchases a generic "one size fits all" mouthpiece and applies a conventional whitening gel to the mouthpiece. The user then inserts the mouthpiece into his or her mouth and bites down on the mouthpiece so that the whitening process can take place. Although this procedure is much less expensive than professional whitening, it presents a number of difficulties. Because the mouthpiece is not custom fit for the individual user, it is difficult, if not impossible, to obtain a tight, secure fit between the mouthpiece and the user's teeth. This prevents the whitening gel from performing in a optimal manner. Unsatisfactory or incomplete whitening frequently results. Moreover, standard off-the-shelf whitening trays are quite bulky, unattractive, and uncomfortable for the user to wear. It is also difficult for the user to speak clearly while wearing such mouthpieces. As a result, the user is less apt to wear the dental tray for a required duration and is, therefore, less likely to achieve satisfactorily whitened teeth.

SUMMARY OF THE INVENTION

It is therefore an object of this invention to provide an improved dental whitening kit that enables the user to obtain whitened teeth in a manner comparable to professionally whitened teeth but much more conveniently and at a far less expense.

It is a further object of this invention to provide a dental whitening kit that eliminates the time and expense required when visiting a dentist to have teeth professionally whitened.

It is a further object of this invention to provide a dental whitening kit that significantly reduces the time, equipment and labor currently required for a dentist and his staff to perform dental whitening.

It is a further object of this invention to provide a dental whitening kit that employs a lightweight, attractive and comfortable to wear tray that is much more convenient for a person to use than conventional off-the-shelf products.

It is a further object of this invention to provide a dental whitening kit that permits the user to effectively whiten his or her teeth using a custom fitted tray that is virtually as effective as the trays currently manufactured by dental professionals.

It is a further object of this invention to provide a process for allowing a user to perform dental whitening in a quick, simple, convenient and yet highly effective manner.

It is a further object of this invention to provide a dental whitening kit that is comfortable to wear and virtually invisible and which does not interfere with the user's speech.

It is a further object of this invention to provide a dental whitening kit that is much more convenient and comfortable to use than conventional off-the-shelf whitening kits and which therefore encourages more prolonged use and provides for significantly improved teeth whitening results.

It is a further object of this invention to provide a dental whitening kit that exhibits a fit that is significantly improved over the fit provided by conventional off-the-shelf dental whitening trays and which therefore provides much improved dental whitening results.

It is a further object of this invention to provide a dental whitening kit that may be marketed effectively through dental offices as a low cost, effective and preferable alternative to conventional over-the-counter dental whitening kits.

This invention results from a realization that a convenient, effective and low cost dental whitening tray may be manufactured by employing a thin sheet of heat and pressure deformable plastic in conjunction with a mouthpiece in which the sheet is held to form a dental impression in the sheet.

This invention features a dental whitening kit for applying a tooth whitening composition to a user's teeth. The kit includes a mouthpiece having a cavity for receiving the user's teeth. There is a separate and distinct thin sheet composed of a heat and pressure deformable plastic. The sheet is heated to a temperature and for a duration such that the sheet is sufficiently pliable to form a dental impression therein. The sheet is disposed over the cavity of the mouthpiece such that the user bites into the sheet and the cavity to form a tray having an impression of the user's teeth. The mouthpiece and the tray are disengaged from the teeth. The tray is then separated from the cavity of the mouthpiece and receives the tooth whitening composition. The user re-engages the tray with the user's teeth to apply the whitening composition to the teeth.

In a preferred embodiment, the mouthpiece comprises an alginate tray. The cavity may contain a putty for forming a dental impression. The putty may include silicone compression putty. Preferably, the mouthpiece is thick and rigid relative to the sheet. The sheet is preferably about 0.03" thick. The tray may be trimable to generally fit the user's gumline.

This invention also features a process for whitening a person's teeth. A dental mouthpiece having a cavity for receiving the person's teeth is provided. A thin sheet of heat and pressure deformable plastic is also provided. The sheet is heated to a temperature and for a duration such that the sheet is sufficiently pliable to form a dental impression therein. The sheet is engaged with the mouthpiece such that the sheet is disposed over the cavity of the mouthpiece. The sheet and the cavity are bit into with sufficient pressure and for sufficient duration such that a dental impression is formed in the sheet and sheet thereby defines a dental tray. The tray is then released from the cavity of the mouthpiece. A whitening composition is introduced into the tray. The tray is reapplied to the teeth that formed the dental impression such that the whitening composition acts to whiten the teeth.

In a preferred embodiment, the foregoing process includes the step of trimming plastic from the tray before the tray is reapplied to the teeth. This is performed to generally fit the tray to the person's gumline. A dental impression forming substance may be introduced into the cavity before the sheet is engaged with the mouthpiece. The dental impression forming substance again may include silicone compression putty.

The sheet may be heated by immersing the sheet in water in excess of 200° F. Typically, the water is heated to temperature of at least 212° for a duration of 10 seconds.

As an alternative to an alginate or otherwise rigid tray, the mouthpiece may include a heat and pressure deformable plastic. The plastic mouthpiece may be heated into a condition that is sufficiently pliable to form a dental impression therein before the sheet and the cavity are bitten into. The process may further include the step of biting into the cavity of the mouthpiece and forming a dental impression therein before the sheet is engaged with the mouthpiece. The process may also include the step of manually pressing the tray and mouthpiece against the teeth and gums while biting into the tray and cavity.

The invention also features a process wherein both the mouthpiece and the plastic sheet are heated and an impression is formed first in the mouthpiece alone by biting into the cavity of the mouthpiece. The heated plastic sheet is then placed over the cavity and the user bites into the sheet and the cavity in which an impression has already been made. After a predetermined duration, the bite is released and the sheet is removed from the cavity and utilized with whitening composition as previously described.

DETAILED DESCRIPTION OF PREFERRED EMBODIMENTS

Other objects, features and advantages will occur from the following description of a preferred embodiment and the accompanying drawings, in which.

Figure 1:
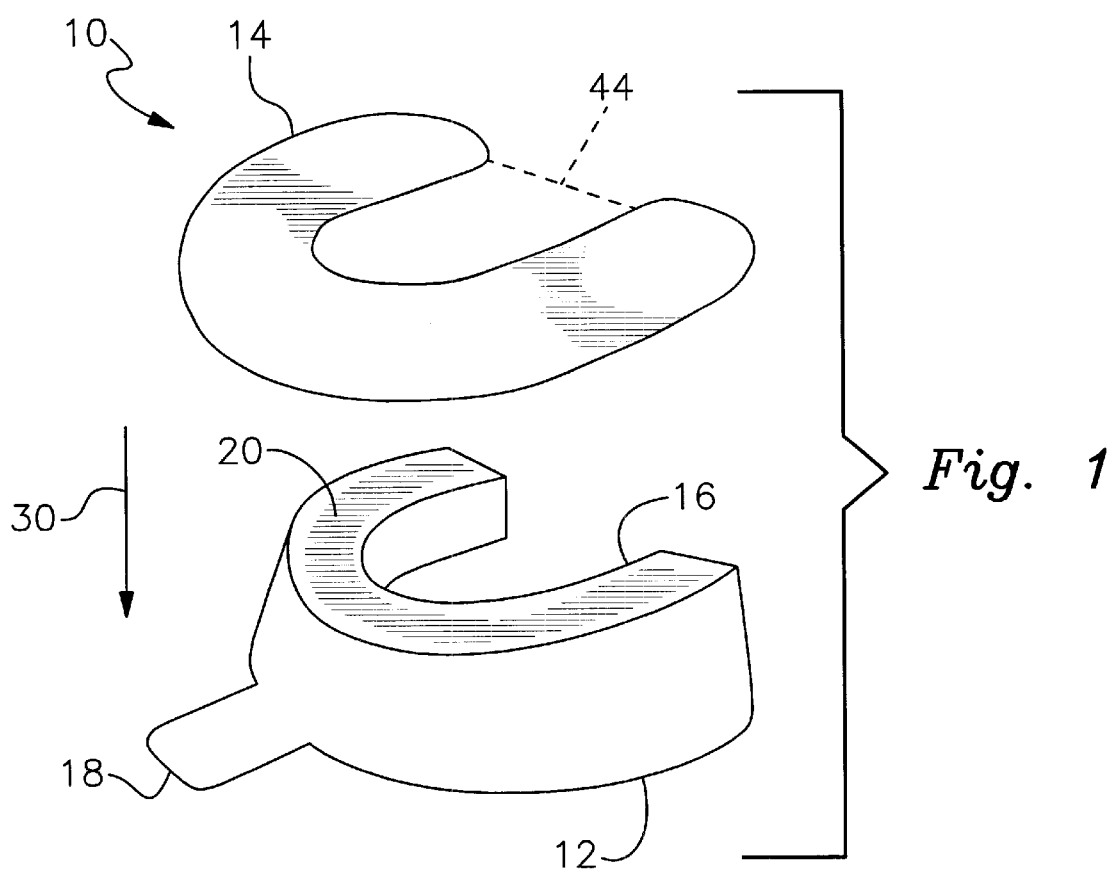
FIG. 1 is a perspective view of a preferred dental whitening kit according to this invention, including a mouthpiece filled with a dental compression compound and a thin plastic sheet that is first engaged with the mouthpiece in a heated condition and then bitten into in order to form a dental whitening gel tray.

There is shown in FIG. 1 a dental whitening kit 10, which comprises a mouthpiece 12 and a separate and distinct thin plastic sheet 14. In this version of the invention, mouthpiece 12 includes a stock alginate tray of the type commonly used for forming dental impressions. The mouthpiece features a cavity 16 that is curved to generally conform to the normal configuration of a person's upper or lower teeth. A handle 18 is attached to the front end of the mouthpiece. This handle facilitates insertion and removal of the mouthpiece to and from the user's mouth.

Mouthpiece 12 is filled with a compound 20 of the type is normally used to form dental impressions. This preferably includes a silicone compression putty, which comprises silicone and an appropriate thickner. Various other dental compression compounds that will be known to those skilled in the art may also be used. Compound 20 is prefilled into cavity 16 of mouthpiece 12 and the mouthpiece is hermetically sealed and provided as a part of kit 10.

Plastic sheet 14 includes a thin sheet of heat and pressure deformable plastic such as polyvinyl. Various other types of plastic materials may be used in accordance with this invention. Sheet 14 preferably has a thickness of about 0.03". The thin plastic sheet may comprise the same material and dimensions presently used for professionally manufactured dental trays. Such material features a very thin, lightweight composition and construction.

Figure 2:
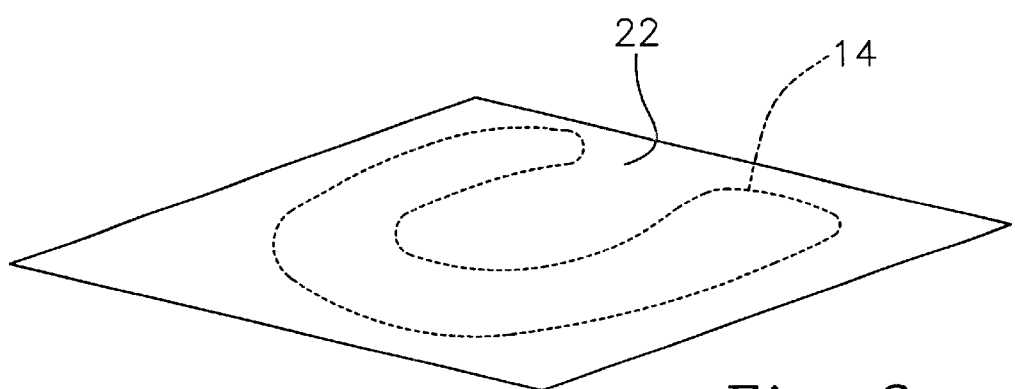
FIG. 2 is perspective view of a preferred thin plastic sheet used in this invention; a segment of the sheet pre-cut to the general shape of the tray and used in the version of the kit shown in FIG. 1 is depicted in phantom.

In FIG. 1, sheet 14 has a curved shape that generally corresponds to the shape of cavity 16 in tray 12. Typically, sheet 14 is cut out of a larger stock piece of plastic such as rectangular sheet 22, shown in FIG. 2. This flat piece of plastic and may have various dimensions. It is not critical, however, that sheet 14 be cut out of a larger sheet 22. In alternative embodiments of this invention, relatively small rectangular or alternatively shaped sheets similar to depicted sheet 22 may be engaged with tray 12 in a manner analogous to that shown for sheet 14 in FIG. 1 and as described further below. In the version shown in FIGS. 1–4, sheet 14 is cut or otherwise pre-formed from sheet 22 or some other stock piece of plastic sheet material. This may be accomplished manually or by machine. Sheet 14 should be cut so that there is sufficient material to drape over the sides of tray 12. This is important so that the thin plastic sheet will adhere to the mouthpiece when a dental impression is made in the plastic sheet in the manner described below.

Typically, kit 10 is sold as a package which includes the hermetically sealed mouthpiece 12 and putty 18, as well as one or more sheets 14, which, as previously stated, may be either in the general shape and size of sheet 14 or larger sheet 22. The kit may also be accompanied by an appropriate whitening composition. That composition may be standard or include a composition yet to be developed. The precise type of whitening composition is not a limitation of this invention. The assembled kit may be sold through various channels including dentist's offices, drug stores and other retail establishments.

Figure 3:
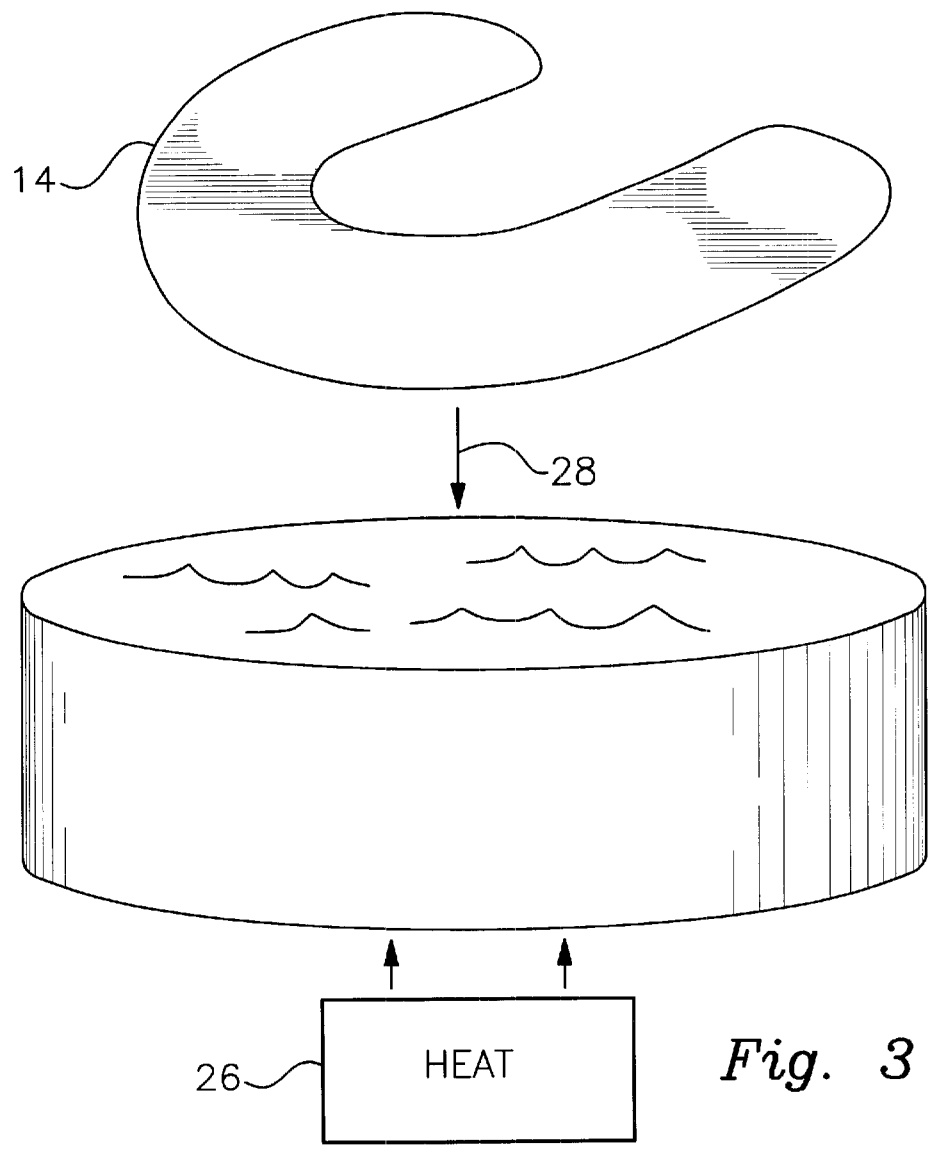
FIG. 3 is a perspective, partly schematic view of the pre-cut plastic sheet being heated in boiling water so that it is sufficiently pliable to form the gel tray.

Kit 10 is designed primarily to be used by individuals at home or at other locations other than the dentist's office. To employ the dental whitening kit, the user opens the kit and removes plastic sheet 14. As shown in FIG. 3, a container of water 24 is heated by a heat source 26. The heat source typically comprises a microwave oven, stove burner or other standard means. Normally, the water in container 24 is heated to or proximate its boiling point. At the very least, the water should be heated to 200°. When the desired temperature is reached, sheet 14 is immersed into the water in the direction of arrow 28. The plastic sheet is allowed to soften within the water for a duration of typically 12 to 30 seconds. The precise time duration and water temperature are not critical limitations of this invention. The temperature and duration should be sufficient so that plastic sheet 14 is rendered sufficiently pliable to form dental impressions in the sheet.

Figure 4:
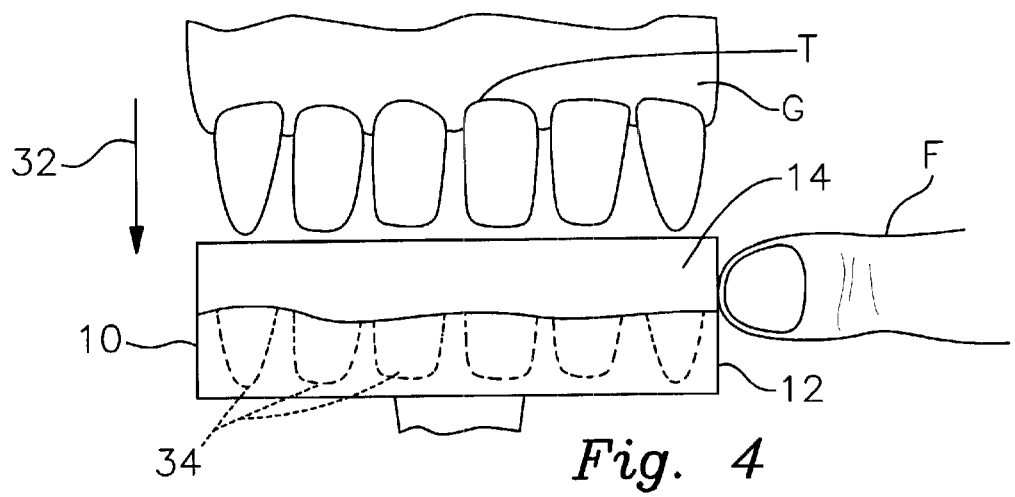
FIG. 4 is an elevational view of the mouthpiece with the plastic sheet engaged over the cavity and positioned beneath a set of teeth to be whitened; the tooth-shaped dental impression formed in the sheet is depicted in phantom; the user's finger is also shown pressing the kit against the teeth after the teeth have bitten into the sheet and cavity in the mouthpiece.

After sheet 14 is heated in the above manner, the sheet is removed from the water, typically by forceps, tongs or other means. The thin plastic sheet is then engaged with mouthpiece 12. As shown in FIG. 1, sheet 14 is lowered onto the mouthpiece in the direction of arrow 30 such that the sheet covers the upper cavity 16 in the mouthpiece. As shown in FIG. 4, the edges of sheet 14 are draped over the sides of mouthpiece 12. The sheet similarly drapes over the inside edges of the mouthpiece. In other versions, a larger piece of plastic such as sheet 22 drapes over the mouthpiece in an analogous fashion. Because the thin sheet has been heated, it adheres to the side walls of the alginate mouthpiece. This enables the sheet to hold its position in the tray so that a precise dental impression is made when the user bites into the mouthpiece.

After the sheet is positioned on the tray in the above described manner, the user inserts the mouthpiece and sheet into his or her mouth. In FIG. 4, the tray is depicted in position for taking a dental impression of the user's upper teeth T. The mouthpiece is inserted so that sheet 14 and underlying cavity 16 (See FIG. 1) are generally aligned under upper teeth T. The user then bites firmly into the sheet 14 and the underlying cavity of mouthpiece 12. This biting action is depicted by arrow 32 in FIG. 4. The teeth T press against sheet 14 and are introduced (e.g. sunk) into compression putty 20 (See again FIG. 1). As depicted in phantom in FIG. 4, an impression 34 of teeth T is formed in sheet 14 within the cavity of mouthpiece 12. The user bites firmly into the mouthpiece and maintains biting pressure for a sufficient duration to produce an acceptable, permanent impression of his/her teeth. This duration is typically about 15 to 30 seconds. While the user continues biting, he/she presses mouthpiece 12 and sheet 14 against his/her teeth T and gum G using one or more fingers F. This helps to provide an optimally tight and secure fit between the sheet and the teeth, and therefore an effective dental impression. This biting and pressing action should continue for at least 15 seconds.

After the user has bit and pressed against sheet 14 and mouthpiece 12 for a desirable duration, the kit is removed from the user's mouth. The user simply dislodges the mouthpiece and the sheet (which now contains the user's dental impression) from his/her teeth T. Because only the polyvinyl sheet engages the teeth, the kit is relatively easy to remove. The user then separates sheet 14 from the cavity of tray 12. This separation is facilitated because the sheet has been impressed into silicone compression putty. This material allows the thin plastic to be released relatively easily from the mouthpiece.

Figure 5:
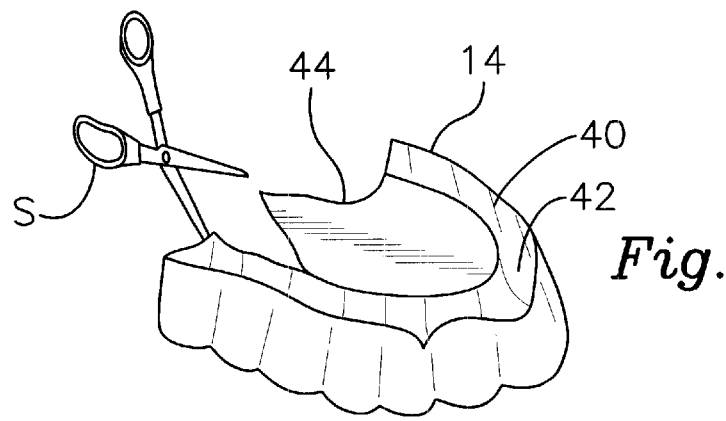
FIG. 5 is a perspective view of a dental tray formed in accordance with the process depicted in FIGS. 1–4; also shown is a pair of scissors trimming the excess plastic carried by the tray.

FIG. 5 depicts sheet 14 after it has been removed from the mouthpiece. Due to heating of the sheet and the pressure previously applied by the user's teeth and finger, an accurate dental impression is formed in the sheet. Specifically, sheet 14 now defines a dental tray 40 having a curved channel 42 that is configured in a manner that closely matches the user's teeth T. In many cases, "excess plastic" 44 will be carried around the edges of channel 42. As used herein, excess plastic refers to any material of the sheet that is not necessary in forming the finished gel tray. In FIG. 5, for example, a large flat section of plastic 44 is shown. That segment is also shown in phantom in FIG. 1. Such a piece generally corresponds to the location of the user's palate. This type of excess piece will normally be present when a sheet 22 (FIG. 2) is used rather than a pre-cut curved sheet 14. Excess segment 44 is included in FIG. 5 merely for illustrative purposes. Normally when a fully preformed curved plastic sheet 14 is employed, the extent of excess plastic will actually be somewhat smaller than what is shown in FIG. 5. In either event, scissors S are employed to trim the excess plastic 44 from the desired tray 40. Trimming can be performed along any of the edges of the tray so that the finished tray fits comfortably in the user's mouth.

Figure 6:
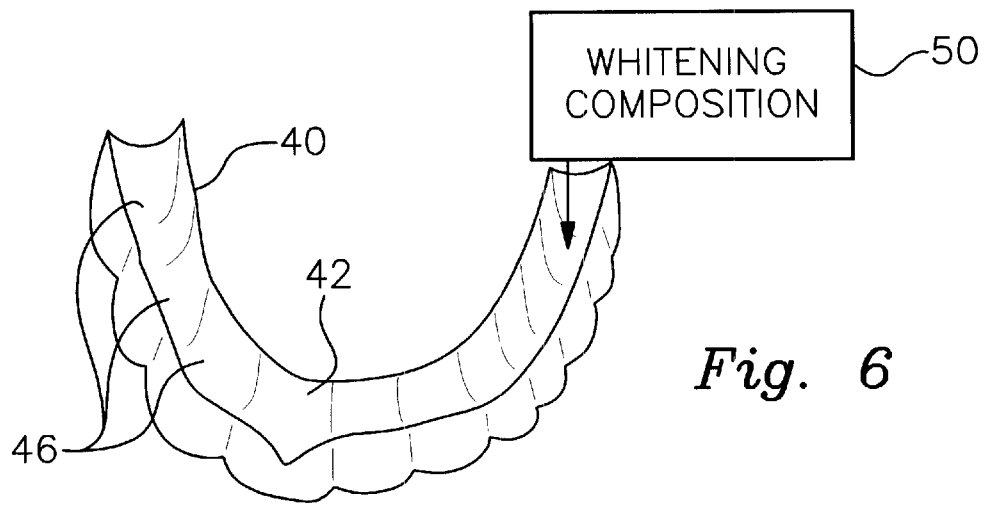
FIG. 6 is a perspective, partly schematic view of a completed dental gel tray manufactured according to the steps shown in FIGS. 1–5; a whitening composition is introduced into the channel of the tray.

When the trimming is completed, a finished tray 40 is provided as shown in FIG. 6. This tray features the curved channel 42, which includes individual pockets 46 corresponding to the user's individual teeth. Completed tray 40 is lightweight and yet very durable. It is comfortable and aesthetically attractive to wear. It does not interfere with the user's speech or appearance.

Figure 7:
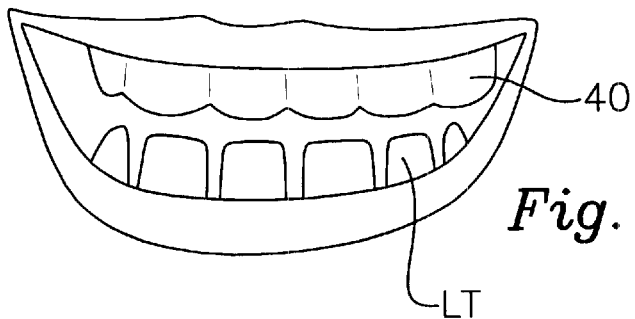
FIG. 7 is an elevational view of a user's mouth with the completed dental gel tray and whitening composition applied to the user's upper teeth.

Whitening gel or other whitening composition 50 is applied in a standard manner within channel 42. The user simply squeezes or otherwise introduces the recommended dosage of the whitening composition into the channel. Tray 40 is then applied to the user's upper teeth in the manner shown in FIG. 7. The user attaches the tray onto the teeth in a manner analogous to various other known brackets and dental trays. The kit of this invention enables tray 40 to conform with and fit securely onto the user's teeth. As previously indicated, tray 40 is attractive and comfortable to wear. It does not interfere with lower teeth LT. It also does not interfere with the user's speech. As a result, the user is much more apt to utilize the tray so that improved dental whitening results are achieved. Additionally, the close fit exhibited by the tray enables intimate contact to be established between the whitening gel and the user's teeth. This also leads to improved whitening results. When the user no longer wishes to wear tray 40, he or she removes it simply by grasping the tray and pulling it off of the teeth in a standard manner.

Figure 8:
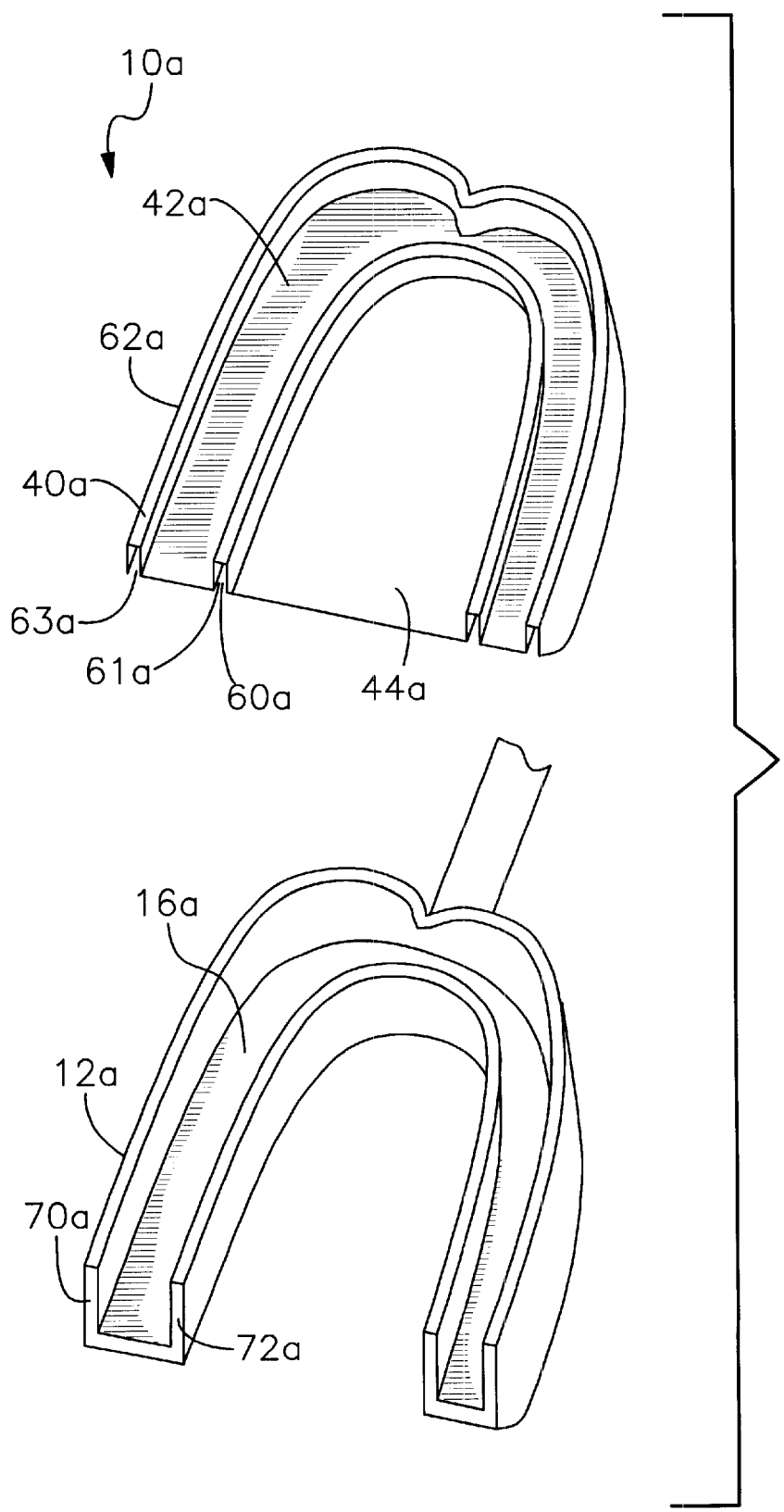
FIG. 8 is a perspective view of the tray and mouthpiece used in an alternative version of this invention.

FIG. 8 depicts an alternative kit 10a according to this invention. When the kit is received by the user, it includes a mouthpiece 12a and a tray 40a that is attached to the mouthpiece. Specifically, mouthpiece 12a includes a channel 16a that generally conforms to the outline of the user's teeth. Tray 40a is again composed of a thin piece of plastic analogous to the plastic sheet in the previously described embodiment. Tray 40a includes curved inner and outer walls 60a and 62a, respectively, and an intermediate channel 42a. Walls 60a and 62a include respective recesses 61a and 63a that extend for the entire length of the walls. The tray is vacuum formed or otherwise manufactured in a standard manner (e.g. using a casting stone or other type of mold). The tray is initially formed with a generic channel, which is configured similar to the outline of a person's teeth but which does not include a dental impression.

Mouthpiece 12a and tray 40a are attached and provided to the end user in an attached manner. Specifically, tray 40a is fitted onto mouthpiece 12a in a generally mating fashion. Recess 63a of tray 40a receives outer wall 70a of mouthpiece 12a. Similarly, inner recess 61a of tray 40a receives inner wall 72a of mouthpiece 12a. Channel 42a of tray 40a fits within cavity 16a of mouthpiece 12a. The tray and the mouthpiece are releasably attached by silicone or a similar agent.

To employ kit 10a, the user heats a container of water in the manner previously described. The water should be boiled or otherwise heated to a temperature and for a duration sufficient to make the tray pliable enough to form a dental impression therein. Typically, after the water is boiled, the tray and the mouthpiece are immersed in the water for at least 25 seconds. The user wets his or her lips with water and places the mating mouthpiece and tray into his or her mouth. The kit is positioned beneath or above the teeth for which an impression is to be taken. The user then bites firmly into channel 42a and underlying cavity 16a. That bite is maintained for at least 15 seconds. While biting, the user presses against the mating mouthpiece and tray in the manner previously shown in FIG. 4. Specifically, the user presses the mouthpiece against the teeth and gums and proceeds from front to back. After this step is completed, the user removes the mouthpiece and tray from his or her mouth and runs the kit under cool water for 10 seconds. This helps the tray to set. Finally, the user pulls the tray out of the mouthpiece. The silicone permits the parts to be conveniently released from one another. Excess plastic, including flat portion 44a, FIG. 8, is trimmed from tray 40a in the manner previously described.

The completed tray 40a contains an virtually exact dental impression of the user's teeth. Once again, the user can apply the whitening composition to the tray and then utilize the tray in the manner previously described to obtain whitened teeth. Tray 40a is comfortable, convenient and aesthetically attractive to use. It obtains improved whitening results in the manner previously described.

Figure 9:
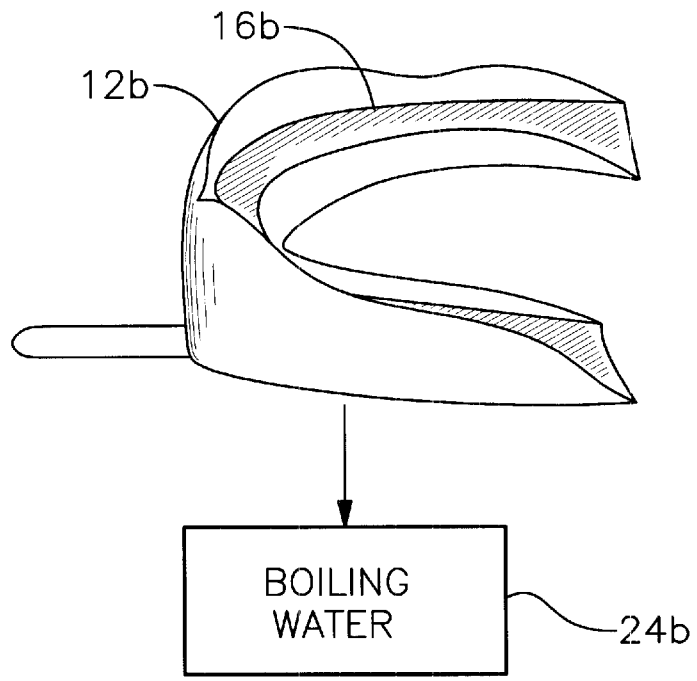
FIG. 9 is a perspective, partly schematic view of a mouthpiece used in still another embodiment of this invention; the mouthpiece is composed of a heat and pressure deformable plastic and is shown being immersed in boiling water.
Figure 10:
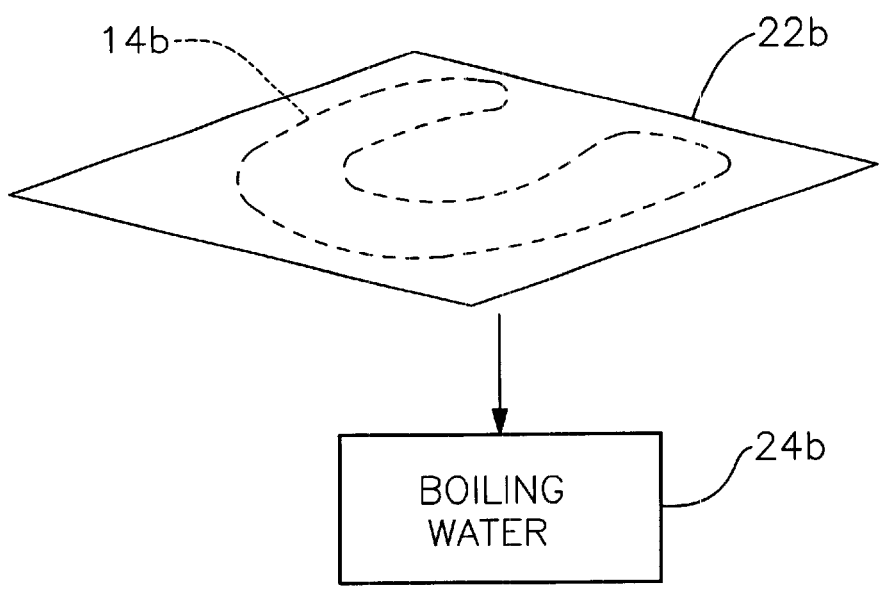
FIG. 10 is a perspective, partly schematic view of the plastic sheet used with the mouthpiece shown in FIG. 9; again, the plastic sheet is depicted schematically as being introduced into boiling water.
Figure 11:
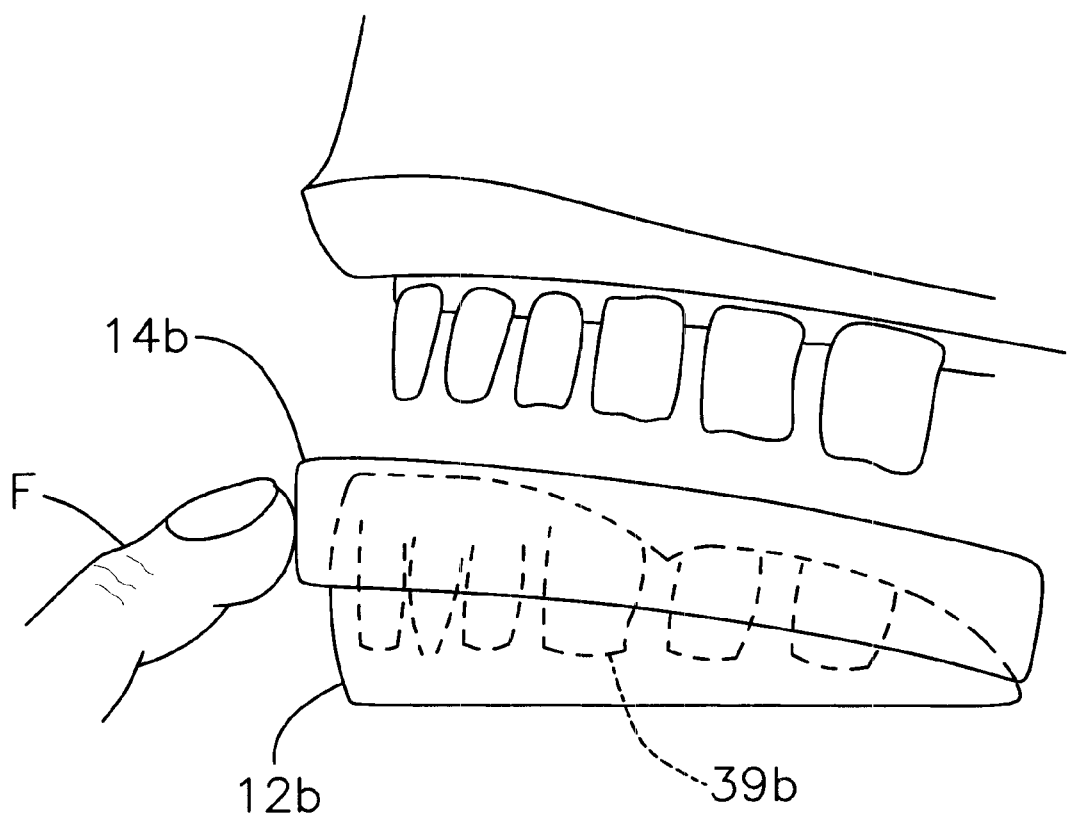
FIG. 11 is an elevational, side view of the mouthpiece and sheet of FIGS. 9 and 10 being bitten into by the upper teeth of the user such that the sheet forms a dental gel tray.

In a third version of the invention, a first dental impression is made in the mouthpiece and then a second impression is made in the thin plastic sheet after the sheet is engaged with the mouthpiece. The operation of this embodiment is illustrated in FIGS. 9–11. Specifically, FIG. 9 depicts a more or less generic mouthpiece 12b that is composed of a heat and pressure deformable plastic. Mouthpiece 12b is typically rather large and bulky and, by itself, does not provide the convenience and effective whitening results achieved through the use of the lightweight and compact dental tray disclosed by this invention.

The third version of the kit also includes a thin plastic sheet 14b, FIG. 10. As in the previously describe embodiments, sheet 14b may have a curved shape that generally conforms to the cavity 16b in mouthpiece 12b. Alternatively, the thin plastic sheet may have a rectangular or other non-curved shape in the manner of sheet 22b, FIG. 10. As previously described, curved sheet 14b may be simply pre-cut out of sheet 22b and used in the following manner with mouthpiece 12b. Otherwise, the thin plastic sheet has a construction that is identical or closely similar to the thin sheet disclosed in the previous embodiments.

In this version, mouthpiece 12b and sheet 14b (or 22b) are sold or otherwise provided to the end user as a pre-packaged unit. However, unlike the second version they are not attached to one another. To utilize the kit, the user first immerses mouthpiece 12b in boiling water 24b, FIG. 9. The mouthpiece is boiled or otherwise heated to a sufficient temperature and for a sufficient duration such that it is pliable enough to form dental impressions therein. As in the previous embodiments, this time can be anywhere from 12 to 30 seconds. After heating of the mouthpiece is completed, the user removes the mouthpiece from the water and inserts it into his or her mouth in a conventional manner. The user bites down into the cavity of the mouthpiece and holds that bite for a sufficient duration such that a dental impression is formed in the mouthpiece. As in the previous embodiments, that dental impression may be of either the user's upper or lower teeth. Because the material in mouthpiece 12b is significantly thicker than the material in the thin plastic sheet 14b, the impression made in the mouthpiece is not as accurate as the impressions that are formed in the thin plastic sheets/trays of this invention. Nonetheless, a preliminary, somewhat precise impression is formed in the mouthpiece.

After the impression is formed in the mouthpiece, the user heats sheet 14b (or larger sheet 22b). This heating may be performed at the same time as mouthpiece 12b is heated. It is typically performed in the same boiling water 24b. In any event, after the initial dental impression is formed in mouthpiece 12b and after sheet 14b is heated sufficiently, the sheet is draped over the mouthpiece such that it is generally aligned with, or at least covers cavity 16b. Essentially, the thin plastic sheet is positioned over the mouthpiece in a manner analogous to that shown in FIG. 1 (although in the third embodiment no compression putty is used). The sheet should be sufficiently large so that is drapes over and adheres to the outer wall of the mouthpiece. The user inserts mouthpiece 12b and sheet 14b into his or her mouth, FIG. 11 and then bites firmly into the cavity of the mouthpiece and the draped plastic sheet. The previously formed dental impressions in the mouthpiece help to form a sharp and accurate dental impression 39b in the plastic sheet. The user holds a firm bite against the mouthpiece and the plastic sheet for at least 15 seconds. At the same time, the user presses mouthpiece 12b and sheet 14b against his or her teeth and gums using fingers F, in the manner previously described. After a predetermined time, the mouthpiece is removed from the user's teeth and the sheet, which now defines a dental tray, is separated from the mouthpiece. The tray now includes pockets that correspond to the user's respective teeth. A very precise dental impression is formed.

Subsequently, excess plastic is trimmed from the completed tray. The tray may then be used with an appropriate dental whitening composition in the manner previously described. This tray provides the advantages that are achieved using the foregoing versions of the kit.

Although specific features of the invention are shown in some of the drawings and not others, this is for convenience only, as each feature may be combined with any and all of the other features in accordance with this invention.

Other embodiments will occur to those skilled in the art and are within the following claims:

What is claimed is:

1. A dental whitening kit for applying a tooth whitening composition to a user's teeth, said kit comprising:
   a mouthpiece having a cavity for receiving the user's teeth, said cavity containing a putty for forming a dental impression therein; and
   a separate and distinct thin sheet composed of a heat and pressure deformable plastic;

said sheet being heated to a temperature and for a duration such that said sheet is sufficiently pliable to form a dental impression therein, said heated sheet being engaged with said mouthpiece and disposed over said cavity such that the user bites into said sheet and said putty contained in said cavity to form in said sheet a tray having an impression of the user's teeth, said mouthpiece and said tray being disengaged from the user's teeth and said tray being separated from said cavity of said mouthpiece and receiving the tooth whitening composition, whereby the user re-engages said tray with the user's teeth to apply the whitening composition to the teeth.

2. The kit of claim 1 in which said mouthpiece comprises an alginate tray.

3. The kit of claim 1 in which said putty includes silicone compression, putty.

4. The kit of claim 1 in which said mouthpiece is thick and rigid relative to said sheet.

5. The kit of claim 1 in which said sheet is less than 0.03" thick.

6. The kit of claim 1 in which said tray is formable to generally fit the user's gumline.

7. A process for whitening a person's teeth comprising:
providing a dental mouthpiece having a cavity for receiving the person's teeth;
introducing a dental impression forming substance into the cavity;
providing a thin sheet of heat and pressure deformable plastic;
heating the sheet to a temperature and for a duration such that the sheet is sufficiently pliable to form a dental impression therein;
engaging the sheet with the mouthpiece such that the sheet is disposed over the cavity of the mouthpiece;
biting into the sheet and the dental impression forming substance in the cavity with sufficient pressure and for sufficient duration such that a dental impression is formed in the sheet and the sheet thereby defines a dental tray;
disengaging the tray and the mouthpiece from the teeth;
releasing the tray from the cavity of the mouthpiece;
introducing a whitening composition into the tray; and
re-engaging the tray containing whitening composition with the teeth that formed the dental impression such that the composition acts to whiten the teeth.

8. The process of claim 7 further including the step of trimming plastic from the tray before the tray is reapplied to generally fit the tray to the person's gumline.

9. The process of claim 7 in which the dental impression forming substance includes silicone compression putty.

10. The process of claim 7 in which the sheet is heated by immersing the sheet in water in excess of 200° F.

11. The process of claim 7 in which said mouthpiece includes a heat and pressure deformable plastic and wherein the mouthpiece is heated into a condition that is sufficiently pliable to form a dental impression therein before biting into the sheet and the cavity.

12. The process of claim 11 further including the step of biting into the cavity of the mouthpiece and forming a dental impression therein before the sheet is engaged with the mouthpiece.

13. The process of claim 7 further including the step of manually pressing the tray and mouthpiece against the teeth and gums while biting.

14. A process for whitening a person's teeth comprising:
providing a dental mouthpiece having a cavity for receiving the person's teeth, said mouthpiece including a heat impression deformable plastic;
providing a thin sheet of heat and pressure deformable plastic;
heating the sheet to a temperature and for a duration such that the sheet is sufficiently pliable to form a dental impression therein;
heating said mouthpiece into a condition that is sufficiently pliable to form a dental impression therein;
biting into the cavity of the mouthpiece and forming a dental impression therein;
engaging the sheet with the mouthpiece after the dental impression is formed in the cavity such that the sheet is disposed over the cavity of the mouthpiece. biting into the sheet and the cavity with sufficient pressure and for sufficient duration such that a dental impression is formed in the sheet and the sheet thereby defines a dental tray;
disengaging the tray and the mouthpiece from the teeth;
releasing the tray from the cavity of the mouthpiece;
introducing a whitening composition into the tray; and
re-engaging the tray containing whitening composition with the teeth that formed the dental impression such that the composition acts to whiten the teeth.

* * * * *